United States Patent [19]

Tino et al.

[11] Patent Number: 5,414,000
[45] Date of Patent: May 9, 1995

[54] ANTIVIRAL PYRINYL SUBSTITUTED TETRAHYDROPYRANS

[75] Inventors: Joseph A. Tino, Robbinsville; Gregory S. Bisacchi, Lawrenceville; Saleem Ahmad, Plainsboro, all of N.J.

[73] Assignee: Bristol-Myers Squibb Co., Princeton, N.J.

[21] Appl. No.: 200,024

[22] Filed: Feb. 22, 1994

Related U.S. Application Data

[62] Division of Ser. No. 9,485, Jan. 25, 1993, Pat. No. 5,314,893.

[51] Int. Cl.$^6$ ............... A61K 31/505; C07D 239/47; C07D 239/54; C07D 239/545
[52] U.S. Cl. ..................... 514/261; 549/417; 544/313; 544/314; 544/317; 544/264; 544/265; 544/276; 544/277; 544/267; 544/254; 514/262; 514/263; 514/265; 514/258; 546/141
[58] Field of Search .......... 514/265, 263, 261; 544/264, 265, 267, 276, 277; 546/141

[56] References Cited

U.S. PATENT DOCUMENTS 3,002,965 10/1961 Fox et al. ............... 544/317
5,013,828 5/1991 Kikuchi et al. ......... 536/23
5,032,680 7/1991 Kawai et al. ........... 536/23
5,059,690 10/1991 Zahler et al. ........... 544/276

FOREIGN PATENT DOCUMENTS 464769 1/1992 European Pat. Off.
468352 1/1992 European Pat. Off.
128395 10/1977 Japan.
296841 6/1989 Japan.
62-4176 7/1963 South Africa.

OTHER PUBLICATIONS

Crane et al., J. Carbohydrates-Nucleoside & Nucleotides, 7(5), 281–296(1980).
Kondo et al., Tetrahedron, vol. 29, pp. 1801–1806 (1973).
Yamazaki et al., Bulletin of The Chem Soc. of Japan, vol. 50(12), 3423–3424(1977).
Ueda et al., Chem. Pharm. Bull. vol. 33(9), 3689–3695(1985).
Yamazaki et al., J. C. S. Perkin I, pp. 1654–1659 (1977).
Nord et al., J. Med. Chem., vol. 30, pp. 1044–1054 (1987).
Antonakis et al., Bulletin De La Societe Chimique De France, pp. 3927–3930 (1969).
Lichtenthaler et al., J. Org. Chem., vol. 41, pp. 600–603 (1976).
Brown et al., Tetrahyedron, vol. 47, pp. 1329–1342 (1976).
Bessodes et al., J. Chem. Soc. Perkins Trans. 1 1990, pp. 3035–3039.
Minamoto et al., J. Chem. Soc. Perkins Trans 1 1990 pp. 3027–3033.
Lau et al., Arch. Pharm, (Weinheim), vol. 324, pp. 83–89 (1991).
Hansen et al., Liebigs Ann. Chem., pp. 1079–1082 (1990).
Augustyns et al., Nucleosides & Nucleotides, 10(1–3), pp. 587–588 (1991).
Van Aerschot et al., Nucleosides & Nucleotides, 10(1–3), pp. 589–590 (1991).

(List continued on next page.)

Primary Examiner—Mukund J. Shah
Assistant Examiner—Matthew V. Grumbling
Attorney, Agent, or Firm—Stephen B. Davis

[57] ABSTRACT

Compounds of the formula

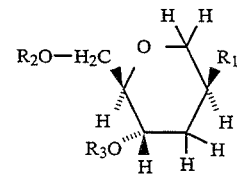

wherein $R_1$ is a substituted purinyl group including pharmaceutically acceptable salts are useful as antiviral agents.

7 Claims, No Drawings

OTHER PUBLICATIONS

Herdewijn et al., Nucleosides & Nucleotides, 10(1-3), pp. 119-127 (1991).
Herdewijn et al., Bull. Soc. Chim. Belg., vol. 99, pp. 895-901 (1990).
Yamasa Shoyu KK, Derwent Abst. 89126 E/42 (1982).
Zorbach et al., Carbohyd. Res., vol. 11, pp. 413-423 (1969).
Warnock et al., Carbohyd. Res., vol. 18, pp. 127-130 (1971).
Grant et al., Biochemistry, vol. 18, pp. 2838-2842 (1979).
Lerner et al., J. Med. Chem., vol. 30, pp. 1521-1525 (1987).
Garner et al., J. Org. Chem., vol. 53, pp. 1294-1298 (1988).
Chow et al., J. Org. Chem., vol. 55, pp. 4211-4214 (1990).
Pederson et al., Heterocycles, vol. 34, pp. 265-272 (1992).
Leutzinger et al., J. Org. Chem., vol. 37, pp. 3695-3703 (1972).
Sanyo Kokusaku Pulp, Derwent Abst. 92-002600/01 (1991).
Pala Kasei Kogyo KK, Derwent Abst. 88-238163/34 (1988).

ANTIVIRAL PYRINYL SUBSTITUTED TETRAHYDROPYRANS

This is a division of application Ser. No. 009,585, filed Jan. 25, 1993 now U.S. Pat. No. 5,314,893.

BACKGROUND OF THE INVENTION

Zahler et al. in U.S. Pat. No. 5,059,690 disclose that bis(hydroxymethyl)tetrahydrofurans having a purinyl or pyrimidinyl substituent possess antiviral activity.

Zahler et al. in European Patent Application 464,769 disclose that 4-hydroxy-5-hydroxymethyl tetrahydrofurans having a purinyl or pyrimidinyl substituent possess antiviral activity.

Takeda in Derwent abstract 87 449Y/49 (Japanese Patent Application 52-128395) disclose antibacterial aristeromycin derivatives including 9β-[2,6-dihydroxy-5β-hydroxymethyl tetrahydropyran-3-yl]hypoxanthine.

Crane et al., J. Carbohydrates-Nucleosides-Nucleotides, 7(5), 281-296 (1980), disclose the synthesis of isonucleosides.

Herdewijn et al., Nucleosides & Nucleotides, 10(1-3), 119-127 (1991), disclose the synthesis of pyranose nucleosides. Herdewijn et al., Bull. Soc. Chim. Belg., 99, 895-901(1990), disclose the synthesis of trideoxydhexopyranosylated and hexenopyranosylated nucleoside analogues as potential anti-HIV agents.

Augustyns et al., Nucleosides & Nucleotides, 10(1-3), 587-588 (1991), disclose sugar modified oligonucleotides.

VanAerschot et al., Nucleosides & Nucleotides, 10(1-3), 589-590(1991) disclose the synthesis and anti-HIV activity of dideoxycytidine analogues containing a pyranose carbohydrate moiety.

Hansen et al., Liebigs Ann. Chem., 1990, 1079-1082, disclose the synthesis of 3'-azido-2', 3'-dideoxy-β-D-arabino-hexopyranosyl nucleosides.

Bessodes et al., J. Chem. Soc. Perkin Trans. 1, 1990, 3035-3039, disclose the synthesis of unsaturated 4'-azido pyranosyl thymines as potential antiviral and anti-HIV agents.

SUMMARY OF THE INVENTION

Antiviral activity is exhibited by compounds of the formula and pharmaceutically acceptable salts thereof. In formula 1 and throughout the specification, the symbols are as defined below.

$X_1$ is hydrogen, amino, $$-NH-\overset{O}{\underset{\|}{C}}-X_7$$

or $-N=CHN\ (X_8)_2$.

$X_2$ is methyl, fluoro, chloro, bromo, iodo, hydroxy, or amino.

$X_3$ is hydrogen, chloro, iodo, or $-O-X_8$.

$X_4$ is amino, chloro, $$-NH-\overset{O}{\underset{\|}{C}}-X_7,$$

or $-N=CHN\ (X_8)_2$.

$X_5$ is hydrogen, methyl, fluoro, chloro, bromo, iodo, hydroxy or amino.

$X_6$ is fluoro, chloro, bromo, iodo, hydrogen, methyl, trifluoromethyl, ethyl, n-propyl, 2-fluoroethyl, 2-chloroethyl or $$\underset{\text{(trans)}}{\overset{H}{\underset{}{\diagdown}}C=C\overset{X_9}{\underset{H}{\diagup}}}$$

$X_7$ is hydrogen, alkyl, substituted alkyl, or alkyl.
$X_8$ is alkyl.

X9 is chloro, bromo, iodo, hydrogen, methyl, or trifluoromethyl.

R₂ and R₃ are independently selected from hydrogen, —PO₃H₂, and

Preferred compounds are those of formula 1 wherein: R₁ is

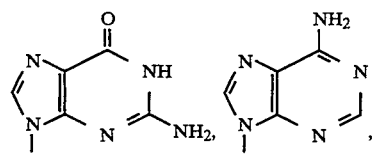

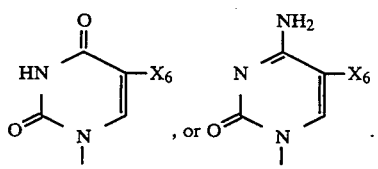

R₂ and R₃ are both hydrogen.

Most preferred compounds of formula 1 are those wherein:
R₁ is

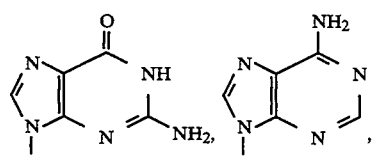

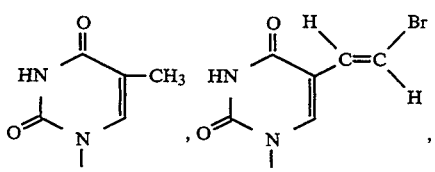

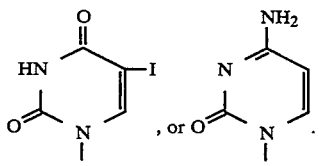

The term "alkyl" refers to both straight and branched chain groups. Those groups having 1 to 10 carbons are preferred. The term "substituted alkyl" refers to such alkyl groups having one or more, preferably one, substituents. Preferred substituents are chloro, bromo, fluoro, iodo, amino, azido, hydroxy, cyano, trialkylammonium (wherein each alkyl group has 1 to 6 carbons), alkoxy of 1 to 6 carbons, aryl and carboxy. The term "aryl" refers to phenyl and phenyl substituted with one, two or three substituents, preferably one. Preferred substituents are alkyl of 1 to 6 carbons, alkoxy of 1 to 6 carbons, chloro, bromo, fluoro, iodo, trifluoromethyl, amino, alkylamino of 1 to 6 carbons, dialkylamino wherein each alkyl is of 1 to 6 carbons, nitro, cyano, alkanoyloxy of 2 to 11 carbons, carboxy, carbamoyl, and hydroxy.

DETAILED DESCRIPTION OF THE INVENTION

The compounds of formula 1, and the pharmaceutically acceptable salts thereof, are antiviral agents that can be used to treat viral infections in mammalian species such as domesticated animals (e.g., dogs, cats, horses and the like) and humans, and avian species (e.g., chickens and turkeys). The compounds of formula 1 wherein R₁ is

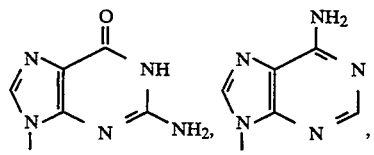

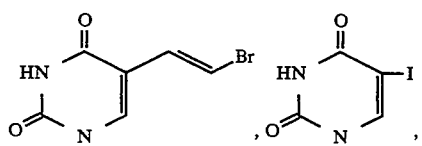

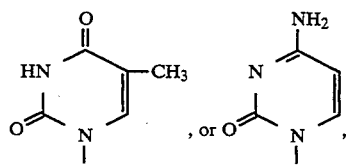

are effective against one or more of the following viruses: herpes simplex virus 1 and 2, varicella-zoster virus, and cytomegalovirus. They are also believed to be active against a variety of other DNA viruses. Exemplary DNA viruses in addition to those named above include other herpes viruses (e.g., Epstein-Barr virus, psedorabies virus, human herpes virus 6, and the like), poxviruses (e.g., vaccinia, monkey pox, and myoma), papovaviruses (e.g., the papilloma viruses), hepititis B virus, and adeno-viruses.

All of the other compounds of formula 1 are believed to be active against one or more of the following viruses: herpes simplex virus 1 and 2, varicella-zoster virus, cytomegalovirus, vaccinia virus, retroviruses, and the other DNA viruses described above.

The compounds of this invention may be administered parenterally (for example, by intravenous, intraperitoneal or intramuscular injection), orally or topically.

The compounds may be administered orally or parenterally in an amount effective to treat the infection. The dosage will, of course, depend on the severity of the infection, but will likely be in the range of about 1.0 to 50 mg/kg of body weight. The desired dose may be administered several times daily at appropriate intervals.

For infections of the eye, or other external tissues, (e.g., mouth and skin), the compositions may be applied to the infected part of the body of the patient topically as an ointment, cream, aerosol, gel, powder, lotion, suspension or solution (e.g., as in eye drops). The concentration of the compound in the vehicle will, of course, depend on the severity of the infection, but will likely be in the range of about 0.1 to 7% by weight.

The compounds of this invention can be prepared from compounds having the formula

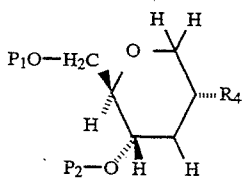
2 wherein R₄ is a leaving group such as chloro, bromo, iodo, an aryl, alkyl, or substituted alkyl sulfonate such as p-toluenesulfonyloxy, methanesulfonyloxy, trifluoromethanesulfonyloxy, etc., and P₁ and P₂ are the same or different and are hydroxy protecting groups such as acyl, benzyl, trityl, substituted trityl (e.g., 4-monomethoxytrityl or 4,4′-dimethoxytrityl) or silyl groups. The term acyl refers to groups of the formula

where R₅ is a straight or branched chain alkyl of 1 to 6 carbons or a phenyl group, preferably R5 is methyl or phenyl. The term silyl refers to silyl protecting groups well known in the art [e.g., t-butyldimethylsilyl, t-butyldiphenylsilyl, (triphenylmethyl) dimethylsilyl, methyldiisopropylsilyl, or triisopropylsilyl]. Alternatively, P₁ and P₂ can be joined to form a 6 to 8 membered ring [e.g., benzylidene acetal, acetonide, or 1,3-(1,1,3,3-tetraisopropyldisiloxanylidene) derivative].

The compounds of formula 2 can be prepared from the corresponding compounds of formula 3 by methods known in the art. For example, treatment of the compounds of formula 3 with p-toluenesulfonyl chloride in pyridine, or methanesulfonyl chloride and triethylamine, or trifluoromethanesulfonic anhydride and pyridine affords the corresponding compounds of formula 2 wherein R₄ is p-toluenesulfonyloxy, methanesulfonyloxy, or trifluoromethanesulfonyloxy, respectively.

Alternatively, the compound of formula 2 wherein R₄ is p-toluenesulfonyloxy can also be prepared from the isomeric compound of formula 6 by known methods [see I. Galynker et al., Tetrahedron Letters, 23, 4461(1982)]. For example, treatment of compound 6 with diethyl or diisopropyl azodicarboxylate in the presence of triphenylphosine, and zinc p-toluenesulfonate affords the compound of formula 2 wherein R₄ is p-toluenesulfonyloxy. Alternatively, the compounds of formula 2 wherein R₄ is p-toluenesulfonyloxy or methanesulfonyloxy can also be prepared from the compound of formula 6 by treatment with p-toluenesulfonic acid or methanesulfonic acid, respectively, in the presence of triethylamine, triphenylphosine, and diethyl or diisopropyl azodicarboxylate in a solvent such as toluene, ether, or dioxane.

The compounds of formula 2 wherein R₄ is chloro, bromo, or iodo can be prepared by treating a compound of formula 6 with a methyltriphenoxyphosphonium halide or methyltriphenylphosphonium halide (i.e., chloride, bromide, or iodide) in a solvent such as dimethylformamide. Alternatively, the compounds of formula 2 wherein R₄ is chloro, bromo, or iodo can be prepared from the compound of formula 6 using triphenylphosphine, diethyl or diisopropyl azodicarboxylate, and a source of halide such as methyl iodide, methyl bromide, or methylene chloride according to methodology known in the art. See, for example, H. Loibner et al., Helv. Chim. Acta., 59, 2100 (1976).

The compounds of formulas 3 and 6 can be prepared from the known compound of formula 4 [See M. Okabe met al., Tetrahedron Letters, 30, 2203 (1989); M. Kugelman et al., J. Chem. Soc. Perkin I, 1113(1976); B. Fraser-Reid et al., J. Amer. Chem. Soc., 92, 6661(1970) for the preparation of the compound of formula 1] as outlined below:

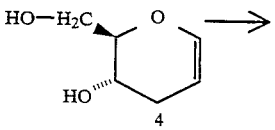

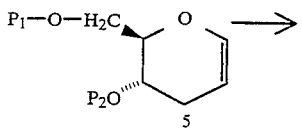

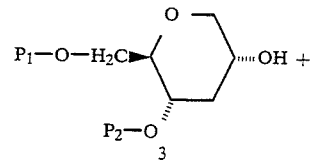

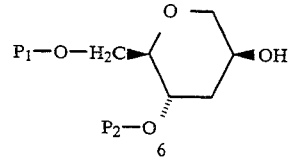

Treatment of the compound of formula 4 with various hydroxyl protecting reagents known in the art affords the compounds of formula 5.

The compounds of formula 5 wherein P₁ and P₂ are both acetyl can also be obtained by the direct reduction of tri-O-acetyl-D-glucal, i.e.

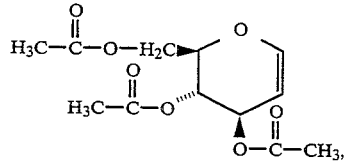

see N. Greenspoon et al., J. Org. Chem., 53, 3723 (1988). Alternatively, this compound of formula 5 can also be obtained by treatment of tri-O-acetyl-D-glucal with sodium borohydride in the presence of Cu(I)Br and tetrakis(triphenylphosphine)palladium(O) in an aprotic solvent such as tetrahydrofuran and/or dimethoxyethane.

Hydroboration of the compound of formula 5 with borane-tetrahydrofuran complex followed by treatment with aqueous sodium bicarbonate and 30% hydrogen peroxide affords a mixture of the compound of formula 3 and the isomeric compound of formula 6 which can be separated, e.g., by chromatography on silica gel.

Treatment of a compound of formula Z with a compound of the formula

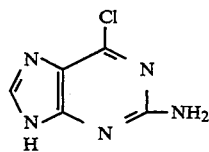

in the presence of a base such as potassium carbonate, sodium hydride, or potassium hydride in an aprotic polar solvent such as dimethylformamide, dimethylsulfoxide, or sulfolane (tetramethylene sulfone) in the optional presence of a metal chelator such as 18-crown-6(1,4,7,10,13,16-hexaoxacyclooctadecane) or 15-crown-5(1,4,7,10,13-pentaoctacyclopentadecane) yields the compound of the formula

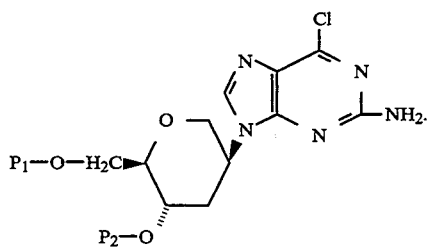

Alternatively, the compound of formula 8 can be prepared by treatment of a compound of formula 2 with a preformed salt of the compound of formula 7 such as the tetra(n-butyl) ammonium salt of the formula

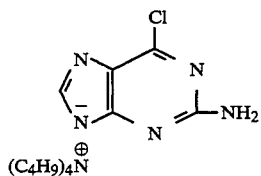

in a solvent such as dichloromethane, acetonitrile, tetrahydrofuran, dimethylformamide, or dimethylsulfoxide.

Removal of the hydroxy protecting groups from the compound of formula 8 yields the products of formula 1 wherein $R_1$ is,

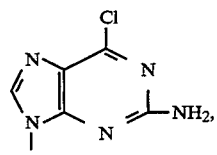

and $R_2$ and $R_3$ are hydrogen. When the protecting group $P_1$ and $P_2$ are acyl groups, they can be removed selectively by treatment with catalytic sodium methoxide in methanol or when $P_1$ and $P_2$ are acetyl groups by treatment with 1,8-diazabicyclo[5.4.0]undec-7-ene (DBU) in benzene [see Baptistella et al., Synthesis, 436 (1989)]. When the protecting groups $P_1$ and $P_2$ in the compound of formula 8 are silyl groups, they can be selectively removed by treatment with a fluoride ion (e.g., tetrabutylammonium fluoride). When the protecting groups $P_1$ and $P_2$ in the compound of formula 8 are benzyl, they can be selectively removed by treatment with boron trichloride.

Treatment of a compound of formula 2 with a compound of the formula

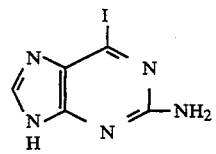

or a preformed salt such as the tetra(n-butyl)ammonium salt of formula 10 under conditions analogous to those used above in the preparation of the compound of formula 8 affords a compound of the formula

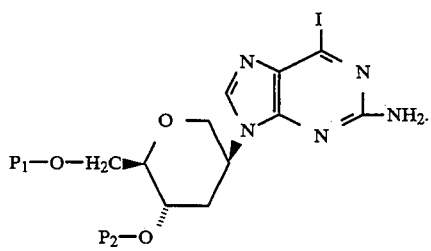

Selective removal of the hydroxy $P_1$ and $P_2$ protecting groups from the compound of formula 11 as described above for the compound of formula 8 yields the product of formula 1 wherein $R_1$ is

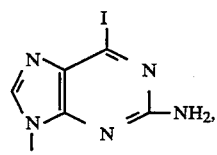

and $R_2$ and $R_3$ are hydrogen.

Reaction of a compound of formula 2 with a protected form of guanine such as a compound of the formula

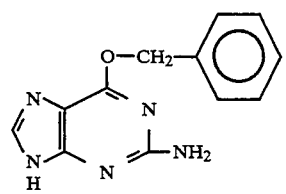

or a preformed salt such as the tetra(n-butyl)ammonium salt of formula 12 under conditions analogous to those used above in the preparation of the compound of formula 8 affords a compound of the formula

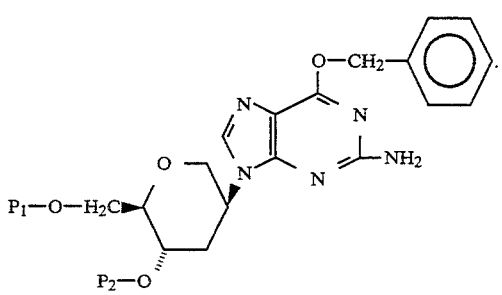

Removal of the hydroxy protecting groups $P_1$ and $P_2$ and the purine 0-benzyl protecting group yields a product of formula 1 wherein $R_1$ is

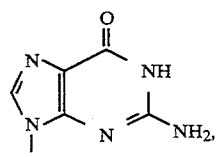

and $R_2$ and $R_3$ are hydrogen.

When the hydroxy protecting groups $P_1$ and $P_2$ in the compound of formula 13 are acyl, they can be selectively removed using catalytic sodium methoxide in methanol or methanolic ammonia. Subsequent removal of the O-benzyl protecting group on the purine moiety can be accomplished by treatment with aqueous alcoholic mineral acid (e.g., aqueous methanolic hydrochloric acid), sodium in liquid ammonia, or by hydrogenolysis (e.g. palladium hydroxide on carbon in cyclohexene and ethanol). Alternatively, the 0-benzyl purine protecting group can be removed first followed by removal of the acyl hydroxy protecting groups.

When the hydroxy protecting groups $P_1$ and $P_2$ in the compound of formula 13 are silyl, they can be selectively removed by treatment with a fluoride ion (e.g., tetrabutylammonium fluoride in tetrahydrofuran). The purine O-benzyl protecting group can then be removed with aqueous alcoholic mineral acid or by hydrogenolysis.

When all of the protecting groups in the compound of formula it are benzyl, removal of all of the benzyl groups can be effected by treatment with sodium in liquid ammonia, hydrogenolysis (e.g., palladium hydroxide on carbon in cyclohexene and ethanol), or by treatment with boron trichloride in methylene chloride.

The product of formula 1 wherein $R_1$ is

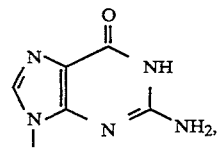

and $R_2$ and $R_3$ are hydrogen, can also be prepared by treatment of the products of formulas 8 or 11 wherein $P_1$ and $P_2$ are acyl with excess sodium methoxide in methanol at reflux followed by acid hydrolysis with, for example, hot aqueous hydrochloric acid. Alternatively, this product of formula 1 can be prepared from the product of formula 1 wherein $R_1$ is

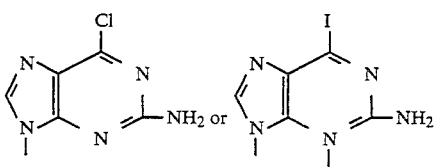

and $R_2$ and $R_3$ are hydrogen by acid hydrolysis (e.g. hot aqueous hydrochloric acid).

Reaction of a compound of formula 2 with methyl-5(4)-(cyanomethyl)-imidazole-4(5)-carboxylate under conditions analogous to those used above in the preparation of the compound of formula 8 followed by sequential treatment with ammonia and aqueous sodium carbonate-ethanol, and removal of the $P_1$ and $P_2$ protecting groups [see Mc Gee et al., Nucleosides & Nucleotides, 9 (6) 815(1990)] affords the product of formula 1 wherein $R_1$ is

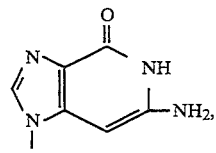

and $R_2$ and $R_3$ are hydrogen.

The product of formula 1 wherein $R_1$ is

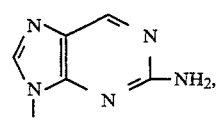

and $R_2$ and $R_3$ are hydrogen can be prepared from a compound of formula 8. For example, when the hydroxy protecting groups $P_1$ and $P_2$ are acyl or silyl groups, the chloro group can first be reduced by hydrogenation (e.g., ammonium formate and palladium on carbon in methanol or ethanol, palladium on carbon in cyclohexane and ethanol, or palladium on carbon, hydrogen and ethanol) and then the protecting groups $P_1$ and $P_2$ can be removed. When $P_1$ and $P_2$ are acyl, the protecting groups can be removed using catalytic sodium methoxide in methanol or methanolic ammonia and when $P_1$ and $P_2$ are silyl they can be removed using a fluoride ion. Alternatively, the $P_1$ and $P_2$ acyl or silyl protecting groups can be removed first and then the chloro group can be reduced. When the hydroxy protecting groups $P_1$ and $P_2$ are benzyl, deprotection and reduction of the chloro group can be accomplished in a single step by hydrogenolysis (e.g., palladium hydroxide on carbon in cyclohexene and ethanol or ammonium formate or formic acid and palladium on carbon in methanol or ethanol).

Alternatively, this product of formula 1 can be prepared by reacting a compound of formula 2 with an optionally protected compound of the formula

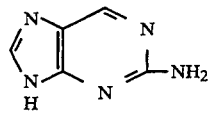

14 or a preformed salt such as the tetra(n-butyl)ammonium salt of an optionally protected compound of formula 14 under conditions analogous to those used in the preparation of the compound of formula 8 followed by removal of the protecting groups by methods known in the art. An optionally protected form of compound 14 can be protected at the amino group by protecting groups such as acyl, trityl or substituted trityl (e.g., 4-monomethoxytrityl or 4,4'-dimethoxytrityl ).

The product of formula 1 wherein $R_1$ is

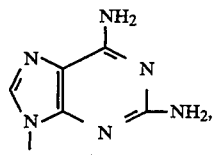

and $R_2$ and $R_3$ are hydrogen can be prepared from the compound of formula 8 by treatment with hot methanolic ammonia according to methods known in the art [see Martin et al., J. Med. Chem., 28, 358(1985)]. When the hydroxy protecting groups $P_1$ and $P_2$ in the compound of formula 8 are acyl, for example, treatment with hot methanolic ammonia results in substitution of the chloro group by an amino group and simultaneous removal of the acyl hydroxy protecting groups. When the hydroxy protecting groups $P_1$ and $P_2$ in the compound of formula 8 are benzyl or silyl groups, replacement of the chloro group by an amino group can be accomplished first, and then the $P_1$ and $P_2$ protecting groups can be removed.

Alternatively, this product of formula 1 can be prepared by reacting a compound of formula 2 with an optionally protected compound of the formula

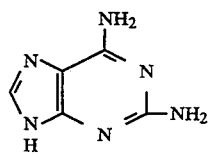

15 or a preformed salt such as the tetra(n-butyl)ammonium salt of an optionally protected compound of formula 15 under conditions analogous to those used above in the preparation of the compound of formula 8 followed by removal of the protecting groups by methods known in the art. An optionally protected form of the compound of formula 15 can be protected at the amino groups by such exemplary groups as acyl, trityl, or substituted trityl.

Products of formula 1 wherein $R_1$ is

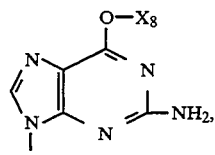

and $R_2$ and $R_3$ are hydrogen can be prepared from the corresponding compounds of formula 8 or products of formula 1 wherein $R_1$ is

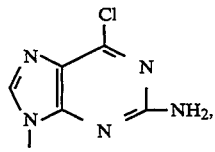

and $R_2$ and $R_3$ are hydrogen by methods known in the art. See, for example, Gerster et al., J. Amer. Chem. Soc., 87, 3752 (1965); Ogilvie et al., Can. J. Chem., 62, 2702 (1984); Harnden et al., J. Med. Chem., 30, 1636 (1987).

Alternatively, this product of formula 1 can be prepared by reacting a compound of formula 2 with a compound of the formula

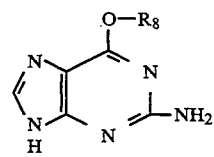

16 or a preformed salt such as the tetra(n-butyl)ammonium salt of formula 16 under conditions analogous to those used in the preparation of the compound of formula 8 followed by removal of the protecting groups by methods known in the art. The compound of formula 16 can be prepared from the compound of formula 7 by methods known in the art. See, for example, Bowles et al., J. Med. Chem., 6, 471 (1963); Mac Coss et al., Tetrahedron Letters, 26, 1815 (1985).

Reaction of the compound of formula 2 with an optionally amino protected form of a compound of the formula

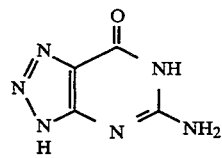

17 or a preformed salt such as the tetra(n-butyl)ammonium salt of an optionally amino protected compound of formula 17 under conditions analogous to those used in the preparation of the compound of formula 8 affords after removal of the protecting groups, the corresponding product of formula 1 wherein $R_1$ is

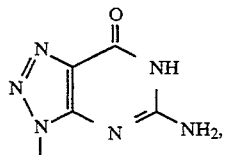

and $R_2$ and $R_3$ are hydrogen. The optional amino protecting groups for the compound of formula 17 include acyl, trityl, and substituted trityl.

Alternatively, reaction of the compound of formula 2 with a compound of the formula

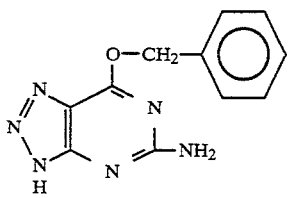

or a preformed salt such as the tetra(n-butyl)ammonium salt of formula 18 under conditions analogous to those used above in the preparation of the compound of formula 8 followed by removal of the protecting groups affords the products of formula 1 wherein $R_1$ is

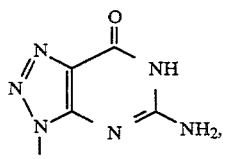

and $R_2$ and $R_3$ are hydrogen.

Additionally, this product of formula 1 can also be prepared by reaction of the compounds of formula 2 with a compound of the formula

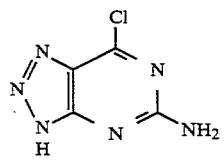

or a preformed salt such as the tetra (n-butyl)ammonium salt of formula 19 under conditions analogous to those used above in the preparation of the compound of formula 8 followed by acid hydrolysis of the chloro group and simultaneous or subsequent removal of the $P_1$ and $P_2$ protecting groups.

Reaction of the compound of formula 2 with a compound of the formula

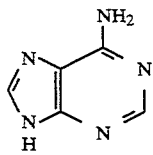

or a preformed salt such as the tetra(n-butyl)ammonium salt of formula 20 under conditions analogous to those used above in the preparation of the compound of formula 8 and subsequent removal of the $P_1$ and $P_2$ protecting groups, yields the corresponding product of formula 1 wherein $R_1$ is

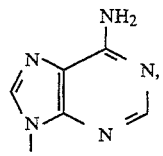

and $R_2$ and $R_3$ are hydrogen.

Alternatively, this product of formula 1 can also be prepared by reaction of the compound of formula 2 with the compound of the formula

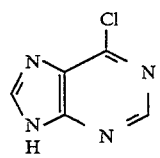

or a preformed salt such as the tetra (n-butyl) ammonium salt of formula 21 under conditions analogous to those used above in the preparation of the compound of formula 8 to afford the corresponding compound of the formula

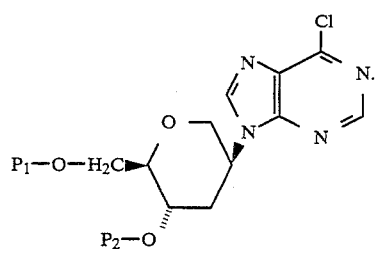

Treatment of the compound of formula 22 with hot ammonia in alcohol (methanol or ethanol) and simultaneous or subsequent removal of the $P_1$ and $P_2$ protecting groups yields the product of formula 1 wherein $R_1$ is

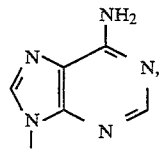

and $R_2$ and $R_3$ are hydrogen.

The product of formula 1 wherein $R_1$ is

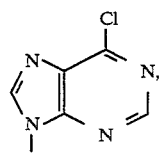

and $R_2$ and $R_3$ are hydrogen can be prepared by selective removal of the $P_1$ and $P_2$ protecting groups from the compound of formula 22 according to the procedures described previously.

Acid hydrolysis (e.g., using hot aqueous hydrochloric acid) or basic hydrolysis (e.g. using aqueous methanolic sodium hydroxide) of the chloro group of the product of formula 1 wherein R₁ is

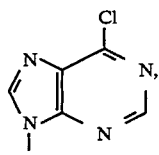

and R₂ and R₃ are hydrogen provides the product of formula 1 wherein R₁ is

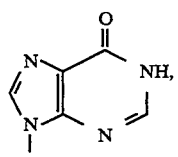

R₂ and R₃ are hydrogen. Alternatively, this product of formula 1 can also be prepared by treatment of the product of formula 1 wherein R₁ is

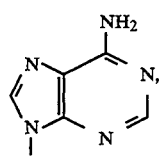

and R₂ and R₃ are hydrogen with adenosine deaminase according to methods known in the art [see Robins et al., *J. Med. Chem.*, 27, 1486(1984); Ogilvie et al., *Can. J. Chem.*, 62, 241 (1984)].

The product of formula 1 wherein R₁ is

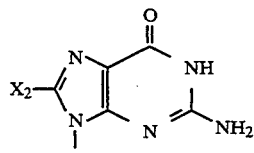

and X₂ is methyl, chloro, bromo, iodo, hydroxy, or amino, and R₂ and R₃ are hydrogen can be prepared from the corresponding products of formula 1 wherein X₂, R₂, and R₃ are hydrogen, by methods known in the art.

The product of formula 1 wherein R₁ is

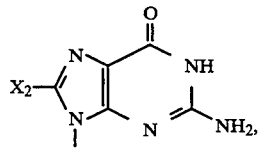

X₂ is fluoro, and R₂ and R₃ are hydrogen can be prepared from the corresponding compounds of formula 1 wherein X₂ is bromo or iodo, and R₂ and R₃ are hydrogen. The amino group can optionally be protected with an acyl protecting group. Treatment with fluoride ion (e.g., sodium or potassium fluoride in a solvent such as dimethylformamide or diethylene glycol, or tetrabutylammonium fluoride in tetrahydrofuran) followed by removal of the optional acyl protecting group using, for example, catalytic sodium methoxide in methanol or methanolic ammonia provides the produce of formula 1 wherein R₁ is

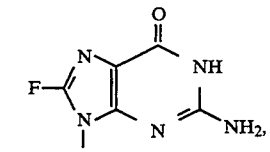

and R₂ and R₃ are hydrogen.

Products of formula 1 wherein R₁ is

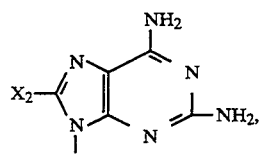

X₂ is methyl, chloro, bromo, iodo, hydroxy or amino, and R₂ and R₃ are hydrogen can be prepared from the corresponding products of formula 1 wherein X₂, R₂, and R₃ are hydrogen using procedures known in the art. The amino groups can be optionally protected by acyl protecting groups.

The product of formula 1 wherein R₁ is

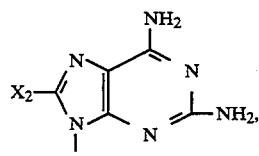

X₂ is fluoro, and R₂ and R₃ are hydrogen can be prepared from the corresponding products of formula 1 wherein X₂ is bromo or iodo, and R₂ and R₃ are hydrogen. The amino groups can be optionally protected with acyl protecting groups. Treatment with fluoride ion (e.g., sodium or potassium fluoride in a solvent such as dimethylformamide or diethylene glycol, or tetrabutylammonium fluoride in tetrahydrofuran) followed by removal of the optionally acyl protecting groups, using, for example, catalytic sodium methoxide in methanol or methanolic ammonia, provides the product of formula 1 wherein R₁ is

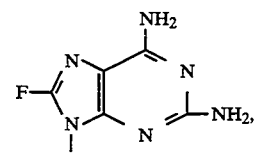

and R₂ and R₃ are hydrogen.

Products of formula 1 wherein R₁ is

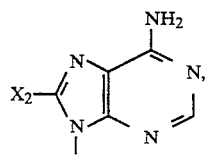

$X_2$ is methyl, chloro, bromo, iodo, or hydroxy, and $R_2$ and $R_3$ are hydrogen can be prepared from the corresponding products of formula 1 wherein $X_2$, $R_2$ and $R_3$ are hydrogen according to procedures known in the art. The amino group can optionally be protected by an acyl protecting group.

The product of formula 1 wherein $R_1$ is

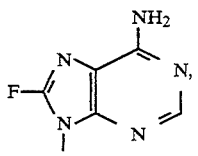

and $R_2$ and $R_3$ are hydrogen can be prepared from a compound of the formula

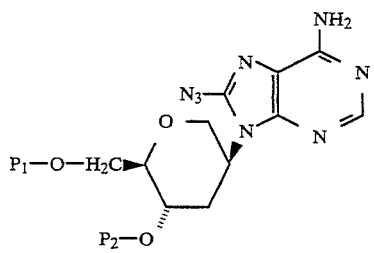

by methods known in the art. The compound of formula 23 can be prepared by known methods from the product of formula 1 wherein $R_1$ is

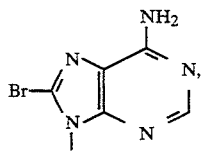

and $R_2$ and $R_3$ are hydrogen. The amino group can optionally be protected with an acyl protecting group.

For general methods of preparing 8-substituted purine nucleosides and nucleoside analogs, see, for example: Robins, et al., *J. Med. Chem.*, 27, 1486 (1984); Holmes et al., *J. Amer. Chem. Soc.*, 86, 1242(1964); Long et al., *J. Org. Chem.*, 52, 2751 (1967); Holmes et al., *J. Amer. Chem. Soc.*, 86, 1772(1965); Ikehara et al., *Tetrahedron*, 26, 4251(1970); Brentnall et al., *Tetrahedron Letters*, 2595(1972); Ikehara et al., *Chem. Pharm. Bull.* 13, 1140(1965); Ikehara et al., *Chem. Commun.*, 1509(1968).

The product of formula 1 wherein $R_1$ is

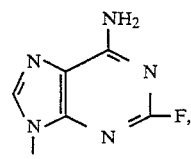

$R_2$ and $R_3$ are hydrogen, can be prepared from the product of formula 1 wherein $R_1$ is

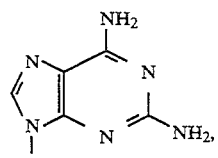

and $R_2$ and $R_3$ are hydrogen according to known procedures. See, for example, Montgomery et al., "Synthetic Procedures In Nucleic Acid Chemistry", Vol.. 1, W. W. Zorbach and R. S. Tipson, Eds., Interscience Publishers (John Wiley & Sons), N.Y., p 205, 1968.

Treatment of a compound of formula 2 with a compound of the formula

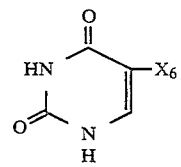

or a preformed salt such as the tetra (n-butyl)ammonium salt of formula 24 wherein $X_6$ is hydrogen, fluoro, methyl, ethyl, n-propyl, 2-chloroethyl or 2-fluoroethyl under conditions analogous to those used in the preparation of the compound of formula 8 yields the compound of the formula

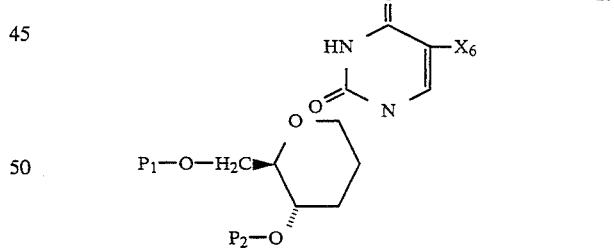

wherein $X_6$ is hydrogen, fluoro, methyl, ethyl, n-propyl, 2-chloroethyl, or 2-fluoroethyl. Removal of the hydroxy protecting groups $P_1$ and $P_2$ provides the products of formula 1. For example, when $P_1$ and $P_2$ are acyl protecting groups, these groups can be removed by treatment with sodium methoxide in methanol or methanolic ammonia. When $P_1$ and $P_2$ are silyl protecting groups, deprotection can be accomplished with fluoride ion. When $P_1$ and $P_2$ are benzyl protecting groups, deprotection can be accomplished by hydrogenolysis (e.g., palladium hydroxide on carbon in cyclohexene and ethanol) or by treatment with boron trichloride.

The compounds of formula 24 wherein $X_6$ is 2-chloroethyl or 2-fluoroethyl can be prepared by methods known in the art [see Griengl et al., *J. Med Chem.*, at 28, 1679(1985) and 30, 1199(1987)].

The product of formula 1 wherein $R_1$ is

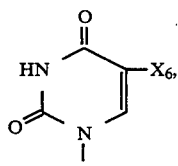

$X_6$ is fluoro, and $R_2$ and $R_3$ are hydrogen can also be prepared by treating the corresponding compounds of formula 1 wherein $X_6$ is hydrogen or the compounds of formula 25 wherein $X_6$ is hydrogen by fluorination with trifluoromethyl hypofluorite using known methods. When the compounds of formula 25 are used, the protecting groups $P_1$ and $P_2$ are acyl protecting groups which are removed after fluorination. The fluorination procedures are described by Robins et al., *J. Amer. Chem. Soc.*, 93, 5277 (1971) and *Chem. Communs.*, 18(1972) and Lin et al., *J. Med. Chem.*, 26 1691(1983).

The products of formula 1 wherein $R_1$ is

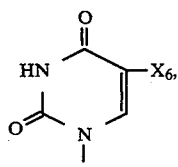

$X_6$ is 2-chloroethyl or 2fluoroethyl, and $R_2$ and $R_3$ are hydrogen can also be prepared from a compound of the formula

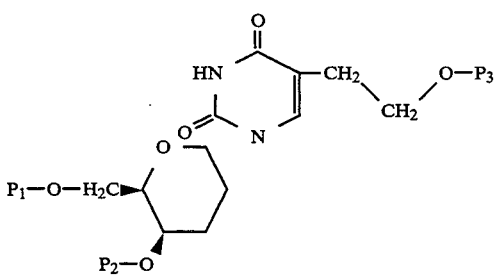

26 wherein $P_3$ is a protecting group which can be selectively removed in the presence of $P_1$ and $P_2$. For example, $P_3$ can be a silyl, trityl or substituted trityl protecting group when $P_1$ and $P_2$ are benzyl or acyl protecting groups. Similarly, $P_3$ can be an acyl or benzyl protecting group when $P_1$ and $P_2$ are silyl protecting groups. Selective removal of $P_3$ yields the corresponding pyrimidindione having a 2-hydroxyethyl substituent. Treatment of this compound with triphenylphosphine-carbon tetrachloride and subsequent removal of the $P_1$ and $P_2$ protecting groups affords the product of formula 1 wherein $R_1$ is

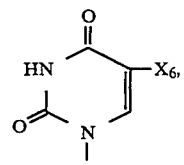

$X_6$ is 2-chloroethyl, and $R_2$ and $R_3$ are hydrogen. Similar treatment using triphenylphosphine-N-bromosuccinimide or triphenylphosphine-N-bromosuccinimide-tetrabutylammonium iodide in place of triphenylphosphine-carbon tetrachloride [see Griengl et. al., *J. Med. Chem.*, 28, 1679(1985)] affords the corresponding pyrimidinedione having a 2-bromoethyl or 2-iodoethyl substituent, respectively. Subsequent treatment with fluoride ion followed by removal of the $P_1$ and $P_2$ protecting groups provides the product of formula 1 wherein $R_1$ is

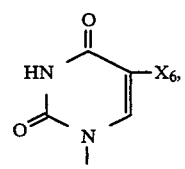

$X_6$ is 2-fluoroethyl, and $R_2$ and $R_3$ are hydrogen. When $P_1$ and $P_2$ are silyl protecting groups, deprotection will occur upon treatment with fluoride ion. Alternatively, these 2-fluoroethyl compounds can be obtained by treatment of a compound of formula 25 wherein $X_6$ is 2-hydroxyethyl with diethylaminosulfur trifluoride followed by removal of the $P_1$ and $P_2$ protecting groups.

The compound of formula 26 can be prepared by reaction of a compound of formula 2 with a compound of the formula

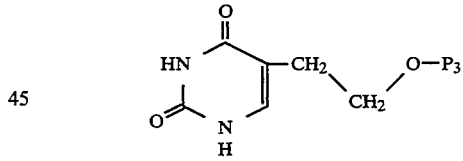

27 or a preformed salt such as the tetra (n-butyl)ammonium salt of formula 27 under conditions analogous to those used above in the preparation of the compound of formula 25 wherein, for example, $X_6$ is hydrogen, methyl, or ethyl. The compound of formula 27 can be prepared from the corresponding free alcohol by methods known in the art.

The products of formula 1 wherein $R_1$ is

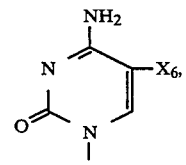

$X_6$ is hydrogen, fluoro, methyl, ethyl, n-propyl, 2-chloroethyl, or 2-fluoroethyl, and $R_2$ and $R_3$ are hydrogen can be prepared from the corresponding compounds of formula 25 wherein $P_1$ and $P_2$ are acyl protecting groups by methods known in the art. See, for example, Wempner et al., "Synthetic Procedures In Nucleic Acid Chemistry", Vol. 1, W. W. Zorbach and R. S. Tipson, Eds., Interscience Publishers, N.Y. p 299, 1968; Lin et al., *J. Med. Chem.*, 26, 1691(1983); Herdewijn et al., *J. Med. Chem.*, 28, 550(1985). Deprotection using methanolic ammonia or sodium methoxide in methanol yields the desired produces of formula 1.

Alternatively, this product of formula 1

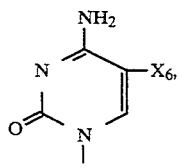

wherein $R_1$ is , $X_6$ is hydrogen, fluoro, methyl, ethyl, n-propyl, 2-chloroethyl or 2-fluoroethyl, and $R_2$ and $R_3$ are hydrogen can be prepared by reacting a compound of formula 2 with the compound of the formula

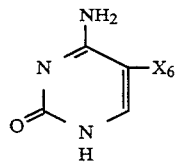

28 or a preformed salt such as the tetra (n-butyl)ammonium salt of formula 28 under conditions analogous to those used above in the preparation of a compound of formula 8 to afford the compound of the formula

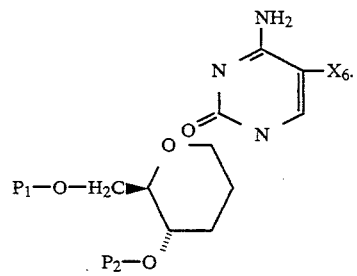

29

Subsequent removal of the $P_1$ and $P_2$ protecting groups affords the desired products of formula 1 wherein $R_2$ and $R_3$ are hydrogen. Optionally, the amino group in the compounds of formula 28 can be protected with an acyl protecting group. Removal of this protecting group can be accomplished using sodium methoxide in methanol or methanolic ammonia.

Alternatively, the product of formula 1 wherein $R_1$ is

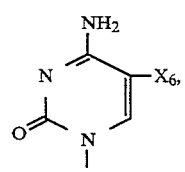

$X_6$ is fluoro, and $R_2$ and $R_3$ are hydrogen can be prepared from the corresponding products wherein $X_6$ is hydrogen by fluorination with trifluoromethyl hypofluorite using methodology known in the art. Fluorination can also be performed on the compounds of formula 29 wherein $X_6$ is hydrogen and $P_1$ and $P_2$ are acyl. Optionally, the amino group can also be protected with an acyl protecting group. After fluorination, deprotection using metholic ammonia or aqueous hydroxide affords the desired products of formula 1. See, for example, Robins et al., *J. Amer. Chem. Soc.*, 93, 5277 (1971) and *Chem. Commun.*, 18(1972); Lin et al., *J. Med. Chem.*, 26, 1691 (1983).

The products of formula 1 wherein $R_1$ is

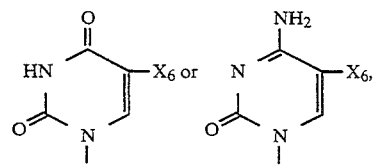

$X_6$ is chloro, bromo, or iodo, and $R_2$ and $R_3$ are hydrogen can be prepared from the corresponding products of formula 1 wherein $X_6$ is hydrogen by methods known in the art. See, for example, "Basic Principals In Nucleic Acid Chemistry", Vol 1, P.O.P. Ts'O, Ed., Academic Press, N.Y., p. 146, (1974); Chang, "Nucleic Acid Chemistry", Part 3, L. B. Townsend and R. S. Tipson, Eds., John Wiley and Sons, N.Y., p 46, (1986).

The products of formula 1 wherein $R_1$ is

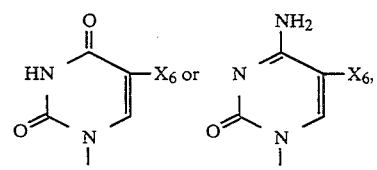

$X_6$ is trifluoromethyl, and $R_2$ and $R_3$ are hydrogen can be prepared from the corresponding products of formula 1 wherein $X_6$ is iodo and the hydroxy and amino groups are protected with acyl protecting groups by treating with trifluoromethyl iodide and copper according to procedures known in the art. Subsequent deprotection using methanolic ammonia or sodium methoxide in methanol yields the desired products of formula 1 wherein $X_6$ is trifluoromethyl. See, for example, Kobayashi et al., *J. Chem. Soc. Perkin* 1, 2755(1980); Lin et al., *J. Med. Chem.*, 26, 1(1983).

The products of formula 1 wherein $R_1$ is

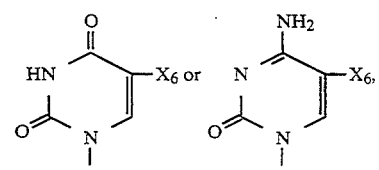

$X_6$ is

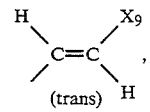

X is chloro, bromo, iodo, hydrogen, methyl, or trifluoromethyl, and $R_2$ and $R_3$ are hydrogen can be prepared from compounds of formula 1 wherein $X_6$ is iodo or —HgCl via organopalladium intermediates. The compounds of formula 1 wherein $X_6$ is —HgCl can be prepared from the corresponding compounds of formula 1 wherein $X_6$ is hydrogen by methods known in the art. See, for example, DeClerq et al., Pharmac. Ther., 26, 1(1984), Perlman et al., J. Med. Chem., 28, 741(1985); Herdewijn et al., J. Med. Chem.; 28, 550(1985); Bergstrom et al., J. Med. Chem., 27, 279(1984).

The products of formula 1 wherein $R_1$ is

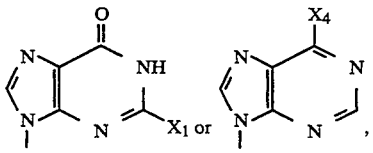

$X_1$ and $X_4$ are

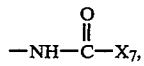

and $R_2$ and $R_3$ are hydrogen can be prepared from the corresponding compounds of formula 1 wherein $R_1$ is

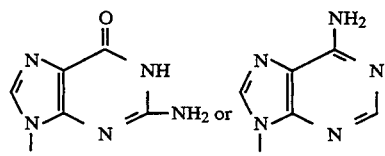

and $R_2$ and $R_3$ are hydrogen by methods known in the art.

The products of formula 1 wherein $R_1$ is

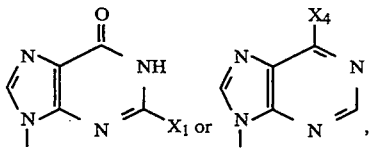

$X_1$ and $X_4$ are —N=CHN$(X_8)_2$, and $R_2$ and $R_3$ are hydrogen can be prepared from the corresponding compounds of formula 1 wherein $R_1$ is

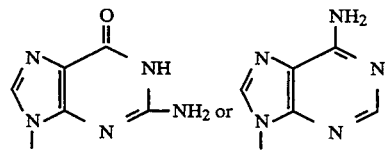

and $R_2$ and $R_3$ are hydrogen by procedures known in the art. See, for example, Holly et al., Collect. Czech. Chem. Commun., 32, 3159(1967); Ogilvie et al., Nucleosides & Nucleotides, 4, 507(1985); Caruthers et al., J, Amer. Chem. Soc., 108, 2040(1986).

The products of formula 1 wherein one or both of $R_2$ and $R_3$ are

can be prepared from the corresponding compounds of formula 1 wherein $R_2$ and $R_3$ are hydrogen by well known acylation procedures. See, for example, "Synthetic Procedures In Nucleic Acid Chemistry", Vol. 1, W. W. Zorbach and R. S. Tipson, Eds., John Wiley and Sons, (1968); "Nucleic Acid Chemistry," Part 1, L. B. Townsend and R. S. Tipson, Eds., John Wiley and Sons, (1978); Ishido et al., Nucleosides & Nucleotides, 5, 159(1986); Martin et al., J. Pharm Sci., 76, 180(1987); Matsuda et al., Synthesis, 385(1986).

The products of formula 1 wherein one or both of $R_2$ and $R_3$ are —PO$_3$H$_2$ can be prepared from the corresponding compounds of formula 1 wherein $R_2$ and $R_3$ are hydrogen by procedures known in the art. See, for example, Schaller et al., J. Amer. Chem. Soc., 85, 3821(1963); Beres et al., J. Med. Chem., 29, 494(1986); Noyori et al., Tetrahedron Letters, 28, 2259(1987); Pfeiderer et al., Helv. Chim. Acta., 70, 1286(1987); "Nucleic Acid Chemistry," Part 2, L. B. Townsend and R. S. Tipson, Eds., John Wiley and Sons, (1978).

The stereochemistry shown for the products of this invention and the intermediates leading to such compounds is absolute. It is drawn to show that in the products of this invention, the absolute stereochemistry is derived from tri-O-acetyl-D-glucal.

The products of formula 1 wherein $R_1$ is

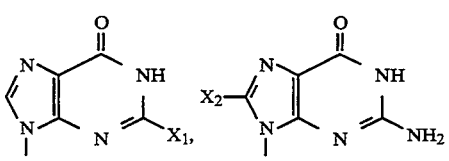

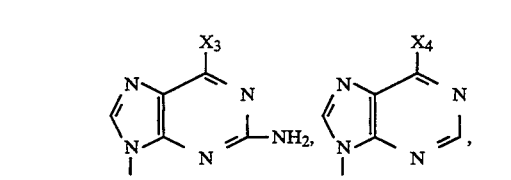

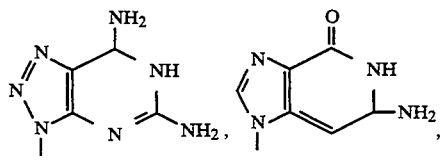

-continued

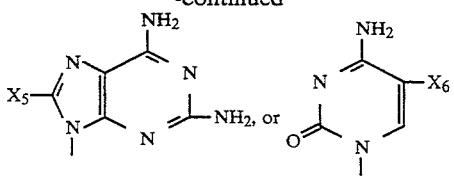

can form acid addition salts with inorganic or organic acids. Illustrative are the hydrohalide salts (e.g., hydrochloride and hydrobromide), alkylsulfonate, sulfate phosphate, and carboxylate salts.

The products of formula 1 wherein $R_1$ is

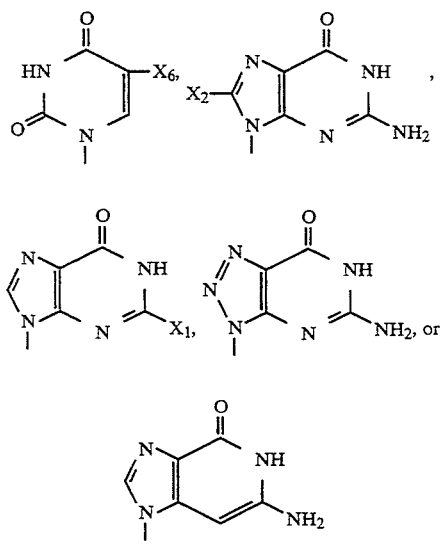

can form basic salts with inorganic and organic bases. Illustrative are alkali metal salts (e.g., sodium and potassium), alkaline earth metal salts (e.g., calcium and magnesium), ammonium and substituted ammonium salts.

The products of formula 1 wherein one or both of $R_2$ and $R_3$ are $-PO_3H_2$ can also form basic salts with inorganic and organic bases as described above.

The following examples are specific embodiments of this invention.

EXAMPLE 1

[3S-(3α, 5β, 6α,]-2-Amino-1,9-dihydro-9-[tetrahydro-5-hydroxy-6-(hydroxymethyl)-2H-pyran-3-yl]-6H-purin-6-one a) (2R-trans)-3-(Acetyloxy)-3,4-dihydro-2H-pyran-2-methanol, acetate (ester)

A suspension of sodium borohydride (3.14 g., 83.0 mmole) in anhydrous tetrahydrofuran (226 ml.) and 1,2-dimethoxyethane (113 ml.) was refluxed for 1.5 hours. After cooling, copper(I)bromide (297 mg., 2.07 mmole) was added and the mixture was refluxed for 2 hours. To this slurry was added tri-O-acetyl-D-glucal (11.30 g., 41.53 mmole) and tetrakis(triphenylphosphine)palladium(O) (2.39 g., 2.076 mmole) at room temperature. The mixture was stirred at room temperature overnight, and then heated at 50° C. for 5 hours. The reaction mixture was then cooled to room temperature, treated at 0° C. with saturated sodium bicarbonate (11 ml.) and 30% hydrogen peroxide (22 ml.). The reaction mixture was diluted with ethyl acetate, washed with saturated sodium bicarbonate, dried and concentrated in vacuo. The residue was purified by column chromatography on silica gel, eluting with ethyl acetate (5% to 10%)hexane with 0.1% triethylamine to give the title compound as a white solid (2.18 g., 10.18 mmole).

b) [2R-(2α, 3β, 5β)]-2-[(Acetyloxy)methyl]tetrahydro-2H-pyran-3,5-diol, 3-acetate A 1.0M borane-tetrahydrofuran complex (9.59 ml., 9.59 mmole) was added dropwise at 0° C. under nitrogen to a dry tetrahydrofuran solution (22 ml.) of the product from part (a) (2.055 g., 9.59 mmole). After 2.5 hours, the mixture was treated with saturated sodium bicarbonate (9 ml.) and 30% hydrogen peroxide (4.3 ml.) at 0°-5° C. and stirred for 2 hours. The reaction mixture was cooled to 0° C., diluted with ethyl acetate, washed with sodium bicarbonate, dried and concentrated in vacuo. The crude product was purified by column chromatography on silica gel, eluting with ethyl acetate (50%, 75%) -hexane, to yield the title compound as a colorless oil (0.654 g., $R_f=0.44$) and the epimeric alcohol, [2R(2α, 3β, 5α)]-2-[(acetyloxy)methyl]tetrahydro-2H-pyran-3,5-diol, 3-acetate, as a white crystalline solid (0.325 g., $R_f=0.34$).

c) [2R-(2α, 3β, 5α)]-3-(Acetyloxy)-5-(2-amino-6-iodo-9H-purin-9-yl) tetrahydro-2H-pyran-2methanol, acetate (ester)

To a mixture of 6-iodo-2-aminopurine (1.21 g., 4.637 mmole) in methylene chloride (12 ml.) at room temperature, was added 1.5M tetra(n-butyl)ammonium hydroxide (2.7 ml., 4.05 mmole). The reaction mixture was stirred for 10 minutes, and the volatiles were removed in vacuo. Methylene chloride (12 ml.) was added to the white residue, and the resulting solution was dried (magnesium sulfate), filtered, and the filtrate was concentrated in vacuo to yield the tetra(n-butyl)ammonium salt of 6-iodo-2-aminopurine as a white residue.

To a stirred solution of [2R-(2α, 3β, 5β)]-2-[(acetyloxy)methyl]tetrahydro-2H-pyran-3,5-diol, 3-acetate (0.633 g., 2.72 mmol) in methylene chloride (12 ml.) at −20° C. was added pyridine (0.33 ml., 4.09 mole) and trifluoromethanesulfonic anhydride (0.504 ml., 3.0 mmole). The reaction was warmed to room temperature. The mixture was diluted with methylene chloride, washed with 10% sulfuric acid, saturated sodium bicarbonate, and water. The organic layer was separated, dried, and concentrated in vacuo to yield crude trifluoromethanesulfonyl product as a dark pink oil.

A solution of this trifluoromethanesulfonyl product in methylene chloride (4 ml.) was added to a mixture of the tetra(n-butyl) ammonium salt of 6-iodo-2-aminopurine in methylene chloride (10 ml.) and the reaction was stirred at room temperature for 16 hours. The mixture was concentrated in vacuo. The residue was dissolved in ethyl acetate (120 ml.) and water (120 ml.), treated for 2 hours with AG-MP 50 cation resin (sodium+ form, 30 g.), and filtered through Celite ®. The crude product was purified by column chromatography on silica gel, eluting with ethyl acetate (50%,75%,100)-hexane, to yield the title compound as a foamy yellow solid (0.587 g., 1.235 mmole).

d) [3S-(3α, 5β, 6α)]-2-Amino-1,9-dihydro-9-[tetrahydro-5-hydroxy-6-(hydroxymethyl)-2H-pyran-3-yl]-6H-purin-6-one Sodium methoxide solution (0.43M, 4.22 ml.) was added to a solution of the product from part (c) (0.58 g., 1.2 mole) in methanol (5 ml.). The mixture was stirred at room temperature for 45 minutes and then refluxed for 5 hours. After cooling to room temperature, the pH of the mixture was adjusted to 7.0 by the addition of 1N hydrochloric acid (1.4 ml.), and concentrated in vacuo. Additional 1N hydrochloric acid (2.5 ml.) was added to the residue and this mixture was heated at 50° C. for 18 hours and then at 85° C. for 3 hours. The reaction mixture was cooled to room temperature, diluted with water, and the pH adjusted to 7.0 by the addition of 3N sodium hydroxide (0.8 ml.). The mixture was concentrated in vacuo and the residue was subjected to a CHP-20 column, eluting with a continuous gradient (water to 25% acetonitrile in water), to afford a yellow residue. This crude product was triturated in methylene chloride, recrystallized from hot water, and treated with activated charcoal to yield 48 mg. of the title compound as white crystals; $[\alpha]_D = -3.46°$ (c=0.0866, dimethylsulfoxide).

$^1$H NMR (270 MHz, DMSO): δ10.57 (s, 1H,—NH); (s,1H,C8H); 6.47 (s,2H, —NH$_2$); 4.92 (d, J=5.28, 1H); 4.67–4.62 (t,J=5.86, 1H); 4,52 (s, 1H); 4.06(d,J=2.34,1H); 3.83–3.78 (dd,J=2.34,12.3,1H); 3.66 (m, 1H); 3.5 (m, 1H); 3.16 (m, 1H); 2.51 (m, 1H); 2.20 (m, 1H); 1.85–1.79 (m, 1H) . 1. R. (KBr pellet): 3435, 3194,2648,2903,1697,1639, 1606,1398,1180,1066 cm$^{-1}$ Anal. calc'd. for $C_{11}H_{15}N_5O_4$. 0.36 H$_2$O:

C, 45.90; H, 5.51; N, 24.33 Found: C, 46.07; H, 5.06; N, 24.16.

EXAMPLE 2

[2R-(2α, 3β, 5α)]-5-(6-Amino-9H-purin-9yl)tetrahydro-3-hydroxy-2H-pyran-2-methanol a) [2R-(2α,3β, 5β)]-2-[(Acetyloxy)methyl]tetrahydro-2H-pyran-3,5-diol, 3-acetate, 5-(4-methylbenzenesulfonate)

p-Toluenesulfonyl chloride (1.78 g., 9.35 mole) was added to a solution of [2R-(2α, 3β, 5β)]-2-[(acetyloxy)methyl]tetrahydro-2H-pyran-3,5-diol, 3-acetate (1.085 g., 4.67 mole) in dry pyridine (25 ml. ) and heated at 70° C. for 22 hours. The brown solution was diluted with ethyl acetate (100 ml. ) and washed once with water and saturated sodium bicarbonate. The organic layer was dried over anhydrous magnesium sulfate, and the solvent was removed in vacuo. The crude oil was purified by silica gel flash chromatography, eluting with ethyl acetate (5%,10%,15%,20%)-hexane, to afford 1.14 g. of the title product as a yellow oil.

b) [2R-(2α, 3β,5α)]-5-(6-Amino-9H-purin-9-yl) tetrahydro-3 -hydroxy-2H-pyran-2 -methanol To a solution of the product from part (a) (1.10 g., 2.654 mmole) in dry dimethylformamide (50 ml.)was added adenine (1.07 g., 7.96 mmole) and flame dried potassium carbonate (0.55 g., 3.98 mole). The mixture was heated overnight at 100° C. The dimethylformamide was removed in vacuo and the crude product was preadsorbed onto silica gel and applied to a column of silica gel packed in chloroform. Elution was carried out with methanol (1%,2.5%,5%,10%,15%)-chloroform giving the desired diacetyl derivative as a major product (124 mg.) and a monohydroxy compound as a minor product (47 mg.). These two compounds were recombined (0.141 g., 0.373 mmole), taken up in methanol (15 ml.) and treated with sodium methoxide solution (0.75 M in methanol, 0.497 ml.) with stirring at room temperature. Additional sodium methoxide (50 μl ) was added and stirred for 15 minutes. The pH of the solution was adjusted to 7.0 by the addition of 2.5% hydrochloric acid. The solvent was removed in vacuo to yield a white residue. The crude product was subjected to a CHP-20 column and eluted with a continuous gradient (water to 25% acetonitrile-water) affording 86 mg. of the title product as a white solid following lyophilization from water; m.p. 105° C. (decomp.); $[\alpha]_D = +21.1°$ (c=0.2036, ethanol). $^1$H NMR (270 MHz, DMSO): δ8.28 (s, 1H); 8.13 (S, 1H); 7.21(s,2H); 4.90 (d,J=5.28,1H); 4.77(s,1H); 4.65(t,J=5.86,1H); 4.19 (d,J=12.31,1H); 3.87 (d,J=2.34,1H); 3.65 (m, 1H); 3.52(m,2H); 3.20 (m, 1H); 2.30 (d,, J=1.75,1H); 1.89 (m, 1H) . IR (KBr Pellet): 3422,2926,1643,1601,1304,1065 cm$^{-1}$. Anal. calc'd. for $C_{11}H_{15}N_5O_3$. 1.18 H$_2$O:

C, 46.11; H, 6.11; N, 24.44 Found: C, 46.44; H, 5.73; N, 24.11.

EXAMPLE 3

[3S-(3α, 5β, 6α)]-4-Amino-1-[tetrahydro-5-hydroxy-6-(hydroxymethyl) -2H-pyran-3-yl]-2-(1H) -pyrimidinone a) [3S-(3α, 5β, 6α)]-1-[5-(Acetyloxy)-6-[(acetyloxy) methyl]tetrahydro-2H-pyran -3-yl]-2,4 (1H, 3H) -pyrimidinedione A 1.5M tetra (n-butyl) ammonium hydroxide solution (8.94 ml., 13.40 mmole) was added to a suspension of uracil (1.715 g., 15.32 mmole) in dimethylformamide (3 ml. ). The mixture was stirred for 10 minutes, and the dimethylformamide was removed in vacuo. Additional dimethylformamide (25 ml. ) was added to the white residue and removed in vacuo. This process was repeated four times, and the resulting tetra (n-butyl) ammonium uracil salt was dried under vacuum (0.1 mm) at 50° C. overnight.

[2R-(2α, 3β, 5β)]-2-[(Acetyloxy)methyl]-tetrahydro-2H-pyran-3,5-diol, 3-acetate, 5-(4-methylbenzenesulfonate) (0.74 g., 1.915 mmole) in dimethylformamide (3 ml.) was added to a solution of the above tetra(n-butyl ) ammonium uracil salt in dimethylformamide (5 ml.) and the suspension was stirred at 75° C. for 2 hours. Acetic acid (773 μl.) was added and the reaction mixture was concentrated to dryness. The residue was dissolved in ethyl acetate (200 ml.) and water (200 ml.), treated with stirring for 2 hours with AG-MP 50 cation resin (sodium+ form, 50 g.) and filtered. The organic phase was isolated and the aqueous phase saturated with sodium sulfate, extracted with ethyl acetate, and the combined organic layers were dried over anhydrous magnesium sulfate and concentrated in vacuo to yield a yellow residue. The residue was taken up in methylene chloride to form a suspension, filtered, and the filtrate concentrated in vacuo to yield the crude product as a yellow oil. This oil was subjected to flash chromatography (silica gel, 0% to 2% ethanol in ethyl acetate) affording 104 mg. of the title product as a gummy white solid.

b) [3S-(3α, 5β, 6α)]-4-Amino-1-[tetrahydro-5-hydroxy-6-(hydroxymethyl]-2H-pyran-3-yl]-2(1H)]-pyrimidinone The product from part (a) (98.0 mg., 0.30 mmole) was dissolved in dry pyridine (4.5 ml.) and p-chlorophenyl dichlorophosphate (171 μl., 1.05 mole) was added with stirring under argon. The reaction mixture was stirred at room temperature for 10 minutes, 1,2,4-triazole (145 mg., 2.1 mole) was added, and the resulting mixture was stirred at room temperature for 4 days and concentrated in vacuo. The residue was dissolved in methylene chloride, and washed once with water and saturated sodium bicarbonate. The aqueous layers were saturated with sodium sulfate and extracted with methylene chloride.

The combined organic phase was dried over anhydrous magnesium sulfate and concentrated in vacuo.

The resulting triazole intermediate was dissolved in dioxane (2.7 ml.), treated with 29% ammonium hydroxide (2.7 ml.), and stirred at room temperature for 24 hours. The reaction mixture was concentrated in vacuo, dissolved in methylene chloride, and washed with water and 2.5% sodium hydroxide solution. The organic layer was extracted three times with water. The combined aqueous layers were washed once with methylene chloride, and the pH adjusted to 7.0 with 2.5% hydrochloric acid. The aqueous layer was concentrated in vacuo, and the residue added in water to a CHP-20 column and eluted with a continuous gradient (water to 10% acetonitrile-water). The desired product was obtained as an orange residue which was dissolved in water, decolorized by the addition of activated charcoal, and filtered to afford a clear solution. Further impurities were removed by dissolving the residue in isopropanol and filtering out the precipitate. The isopropanol solution was concentrated in vacuo and the residue dissolved in water and lyophilized to yield 43 mg. of the title compound as a white solid; $[\alpha_D = +79.43°$ (C=0.23, methanol). $^1$H NMR (270 MHz, DMSO): $\delta$7.97 (d, J=7.62 Hz, 1H, C5H); 7.09–6.9 (m,2H,—NH$_2$); 5.65 (d, J=7.03 Hz, 1H, C5H); 4.91 (d, J=5.28 Hz, 1H, OH); 4.58 (t, J=5.86 Hz, 1H, OH); 4.50 (s, 1H); 3.99 (d, J=12.9 Hz, 1H, —CH$_2$); 3.75 (m, 1H, —CH$_2$), 3.7–3.4 (m, 3H); 2.06 (m, 1H, C3'H); 1.67 (m, 1H, C3'H) . IR (KBr pellet) 3400, 3216, 2992, 2878, 1663, 1618, 1479, 1402, 1279, 1067 cm$^{-1}$ Anal. calc'd for C$_{10}$H$_{15}$N$_3$O$_4$. 3.20 H$_2$O:

C, 40.19; H, 7.22; N, 14.06 Found: C, 41.67; H, 5.24; N, 12.58.

EXAMPLE 4

[3S-(3α, 5β, 6α)]-5-Iodo-1-[tetrahydro-5-hydroxy-6-(hydroxymethyl) -2H-pyran-3-yl]-2,4 (1H, 3H) -pyrimidinedione a) [3S-(3α,5β, 6α)]-1-[Tetrahydro-5-hydroxy-6-(hydroxymethyl)-2H-pyran-3-yl]-2,4(1H, 3H)-pyrimidione

[3S-(3α, 5β, 6α)]-1-[5-(Acetyloxy)-6-[(acetyloxy)methyl]tetrahydro-2H-pyran-3-yl]-2,4(1H,3H)-pyrimidinedione (0.230 g., 0.7055 mmole) was taken up in methanol (40 ml.) and treated with sodium methoxide solution (0.311M in methanol, 1.134 ml.) with stirring at room temperature for 1 hour. The pH of the solution was adjusted to 7.0 by the addition of 2.5% hydrochloric acid. The solvent was removed in vacuo to yield a white residue. The crude product was subjected to a CHP-20 column and eluted with a continuous gradient (water to 20% acetonitrile-water) affording 163 mg. of the title compound as a white solid.

b) [3S-(3α, 5β, 6α)]-5-Iodo-1-[tetrahydro-5-hydroxy-6-(hydroxymethyl)-2H-pyran-3-yl]-2,4(1H, 3H)-pyrimidinedione A mixture of the product from part (a) (0.138 g., 0.569 mmole), iodine (0.217 g., 0.854 mmole), and 0.8 N nitric acid (0.711 mi., 0.568 mmole) in dioxane (12 ml.) was heated at reflux for 24 hours. Additional nitric acid (1.14 ml., 1.138 mmole) was added and heating continued for 45 minutes. The mixture was then cooled to room temperature, the pH was adjusted to 7.0 by the addition of saturated sodium bicarbonate, and the mixture was then concentrated to dryness in vacuo. The crude product was subjected to a CHP-20 column, and eluted with a continuous gradient (water to 62% acetonitrile-water). Appropriate fractions were combined and concentrated in vacuo affording a yellow solid. The residue was taken up in water, lyophilized and then recrystallized from hot water to give 0.162 g. of the title product as white crystals; m.p. 210°–212° C. (decomp.); $[\alpha]_D = +12.08°$ (C=0.21, methanol).

$^1$H NMR (270 MHz, DMSO) $\delta$: 5:11.67 (s,1H,—NH); 8.41 (s, 1H,C6H); 4.93 (d, J=5.28 Hz, 1H, —OH); 4.70 (t, J=5.28, 1H, —OH); 4.49 (s, 1H, C2'H); 4.05 (d, J=12.9 Hz, 1H, —CH$_2$); 3.74 (dd, J=3.52, 12.9 Hz, 1H, —CH$_2$); 3.65 (m, 1H); 3.56 (m, 1H); 3.54 (m, 1H); 3.13 (m, 1H); 2.12 (m, 1H, C3'H); 1.72 (td, J=4.69, 11.14 Hz, 1H, C3'H) . IR (KBr pellet) 3468, 2961, 1709, 1645, 1458, 1414, 1296 cm$^{-1}$. Ana l. calc'd for C$_{10}$H$_{13}$IN$_2$O$_5$. 1.55 H$_2$O:

C, 30.33; H, 4.10; N, 7.07 Found: C, 30.67; H, 4.15; N, 6.73.

EXAMPLE 5

[3S-(3α, 5β, 6α)]-5-Methyl-1-[tetrahydro-5-hydroxy-6-(hydroxymethyl)-2H-pyran-3-yl]-2,4 (1H, 3H)-pyrimidinedione a) [3S-(3α, 5β, 6α)]-1-[5-(Acetyloxy) -6-[(acetyloxy)methyl]tetrahydro-2H-pyran-3-yl]-5-methyl-2,4-(1H. 3H) -pyrimidinedione 1.5M Tetra(n-butyl)ammonium hydroxide (4.22 ml., 6.335 mole) was added to a suspension of thymine (0.913 g., 7.24 mole) in dimethylformamide (15 ml. ). The mixture was stirred for 10 minutes, and the dimethylformamide was removed in vacuo. Additional dimethylformamide (20 ml. ) was added to the white residue, and removed in vacuo. This process was repeated four times and the residue was dried under a vacuum (0.1 mm) at 50° C. overnight affording the tetra(n-butyl)ammonium salt of thymine.

The above salt was taken up in dimethylformamide (5 ml.) and [2R-(2α, 3β, 5β)]-2-[(acetyloxy)methyl]tetrahydro-2H-pyran-3,5-diol, 3-acetate, 5-(4-methylbenzenesulfonate) (0.35 g., 0.905 mmole) in dimethylformamide (2 ml.) was added to the suspension and stirred at 65° C. for 3.5 hours. Acetic acid (0.365 ml.) was added and the reaction mixture was concentrated in vacuo. The residue was dissolved in ethyl acetate (200 ml.) and water (200 ml.), treated with stirring for 1.5 hours with AG-MP 50 cation resin (sodium + form, 40 g.), and filtered. The organic phase was isolated and the aqueous phase was saturated with sodium sulfate, extracted with ethyl acetate, and the combined organic layers were dried over anhydrous magnesium sulfate and concentrated to dryness. The residue was taken up in methylene chloride forming a suspension. The suspension was filtered, and the filtrate was concentrated in vacuo to yield the crude product as a yellow oil. This oil was flash chromatographed (silica gel 0% to 5% ethanol in ethyl acetate) affording 51 mg. of the titled product as a gummy white solid upon concentration in vacuo of the appropriate fractions.

b) [3S-(3α, 5β, 6α)]-5-Methyl-1-[tetrahydro-5-hydroxy-6-(hydroxymethyl)-2H-pyran-3-yl]-2,4(1H,3H)-pyrimidinedione The product from part (a) (0.50 g., 0.146 mmole) was taken up in methanol (5 ml.) and treated with sodium methoxide solution (0.311M in methanol, 0.236 ml.) with stirring at room temperature for 1.5 hours. The pH was adjusted to 7.0 by the addition of 1% hydrochloric acid, and the solvent removed in vacuo to yield a white residue. The crude product was subjected to a CHP-20 column and eluted with a continuous gradient (water to 25% acetonitrile-water) affording a foamy white solid upon evaporation in vacuo. The residue was taken up in water and lyophilized to yield 26 mg. of the title product as a white solid; m.p. 87°–89° C.; $[\alpha]_D = +8.65°$ (c=0.2, methanol).

$^1$H NMR (270 MHz, DMSO) δ: 5:11.26 (s, 1H, —NH); 7.89 (s, 1H, C6H); 4.90 (d, J=5.27 Hz, 1H, —OH); 4.65 (t, J=6.45 Hz, 1H, —OH); 4.51 (br s, 1H); 4.0 (d, J=12.9 Hz, 1H, —CH$_2$); 3.70 (dd, J=2.93, 12.9 Hz, 1H, —CH$_2$); 3.65–3.56 (m, 3H); 3.15 (m, 1H); 2.05 (m, 1H, C3'H); 1.76 (s, 3H, —CH$_2$); 1.72 (m, 1H, C3'H). IR (KBr pellet) 3410, 3227, 3088, 2884, 1703, 1661, 1267 cm$^{-1}$. Anal. calc'd. for $C_{11}H_{16}N_2O_5$. 1.19 H$_2$O:

C, 47.59; H, 6.67; N, 10.09 Found: C, 47.79; H, 6.57; N, 9.89.

EXAMPLE 6

[3S- [3α(E), 5β, 6α]-5(2-Bromoethenyl)-1-[tetrahydro-5-hydroxy-6-(hydroxymethyl)-2H-pyran -3-yl]2,4 (1H, 3H) -pyrimidinedione a) [3S-[3α(E) ,5β, 6α]]-3-[1,2,3,4-Tetrahydro-2,4-dioxo-1-[tetrahydro-5-hydroxy-6-(hydroxymethyl)-2H-pyran-3-yl]-5-pyrimidinyl]-2-propenoic acid, methyl ester A mixture of palladium (II) acetate (25.77 mg. , 0. 105 mole) , triphenylphosphine (55.29 mg. , 0.218 mmole) and triethylamine (440.7 μl 3.162 mole) in dry degassed dimethylformamide (3 ml. ) was stirred at 70° C. for 15 minutes under argon. To the resulting dark brown mixture was added a solution of [3S-(3α, 5β, 6α)]-5-iodo-1-[tetrahydro-5-hydroxy-6-(hydroxymethyl) -2H-pyran-3-yl]-2,4(1H,3H)-pyrimidinedione (388 mg., 1.054 mmole) in dimethylformamide (3 ml.) followed by methyl acrylate (189.9 μl., 2.108 mole). Heating was continued for 2 hours. The mixture was then cooled to room temperature, filtered over Celite ®, washed repeatedly with additional dimethylformamide, and the combined filtrate was concentrated to dryness. The crude product was subjected to a CHP-20 column and eluted with a continuous gradient (water to 30% acetonitrile-water) affording 271 mg. of the title product as a white solid upon concentration of the appropriate fractions in vacuo.

b) [3S-[3α(E) ,5β, 6α]]-3-[1,2,3,4-Tetrahydro-2,4-dioxo-1-[tetrahydro-5-hydroxy-6-(hydroxymethyl)-2H-pyran 3-yl]-5-pyrimidinyl]-2-propenoic acid The product from part (a) (270 mg., 0.827 mole) was taken up in 2N potassium hydroxide (5.5 ml.) and stirred for one hour at room temperature. The pH was adjusted to 1.7 by the addition of 10% hydrochloric acid (about 4 ml.). The resulting slurry was cooled in an ice-bath and then filtered to yield a white solid. Recrystallization from hot water afforded 191 mg. of the title product in two batches as a white solid.

c) [3S-{3α(E) , 5β, 6α]]-5-(2-Bromoethenyl) -1-[tetrahydro-5-hydroxy-6-(hydroxymethyl)-2H-pyran 3H-pyran-3yl]-2.4 (1H. 3H) -pyrimidinedione Granular potassium bicarbonate (0.142 g., 1.42 mole) was added to a solution of the product from part (b) (148 mg., 0.474 mmole) in dry dimethylformamide (1.6 ml.) and the mixture was stirred at room temperature for 10 minutes. A solution of N-bromosuccinimide (10% in dimethylformamide, 886 μl., 0.497 mole) was added slowly over 15 minutes and the mixture was stirred for 30 minutes. The mixture was filtered, washed repeatedly with additional dimethylformamide, and the combined filtrate was concentrated to dryness. The crude product was subjected to a CHP-20 column and eluted with a continuous gradient (water to 25% acetonitrile-water) affording a white residue upon concentration of the appropriate fractions in vacuo. Recrystallization from hot water afforded 103 mg. of the title product as a white solid; m.p. 180°–183° C. (d) ; $[\alpha]_D = 17.5°$ (C=0.2, methanol) . $^1$H NMR (270 MHz, DMSO) δ: 11.58 (s, 1H, —NH); 8.18 (s, 1H, C6H); 7.24 (d, J=13.49 Hz, 1H, vinyl); 6.88 (d, J=13.48 Hz, 1H, vinyl); 4.91 (d, J=5.27 Hz, 1H); 4.69 (t, J=5.86 Hz, 1H); 4.56 (s, 1H); 4.05 (d, J=12.31, 1H); 3.72 (dd, J=2.94, 12.9 Hz, 1H); 3.69–3.61 (m, 3H); 3.13 (m, 1H); 2.12 (m, 1H); 1.76 (td, J=4.1, 14.07 Hz, 1H) . IR (KBr pellet) 3364, 3306, 3071, 3030, 1709, 1663, 1474, 1439, 1298, 1277, 1074 cm$^{-1}$. Anal. calc'd. for $C_{12}H_{15}BrN_2O_5$. 3.92 H$_2$O:

C, 39.89; H, 4.62; N, 7.75 Found: C, 39.95; H, 3.95; N, 7.69.

EXAMPLE 7

Treatment of Viral Infection In Cell Culture in Vitro

Assays were performed in cell culture systems to determine the concentrations of compounds that are effective in preventing several kinds of viral infections. The assays are described below, and the results presented in Table 1. Abbreviations:

HSV-1 (herpes simplex virus type 1, strain Schooler), HSV-2 (herpes simplex virus type 2, strain 186), VZV (varicella zoster virus, strain ELLEN), HCMC (human cytomegalovirus, strain AD 169). Cell Culture Assays:

HSV-1, HSV-2, HCMV and VZV antiviral assays: Virus was adsorbed to WI-38 cell culture monolayers in 5 well culture plates (Costar, Cambridge, Mass.) for 1 hour prior to addition of maintenance medium containing duplicate dilutions of the test compound. Inhibition of plaque development was evaluated on fixed and stained monolayers after 4 days incubation at 37° C. for HSV-1 and HSV-2, and after 5–7 days incubation at 37° C. for HCMV and VZV. ID$_{50}$ values were determined from the drug concentration which conferred at least a 50% plaque reduction compared to virus controls.

TABLE 1

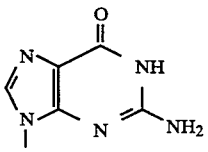

| | ID$_{50}$ (μM) for the following viruses | | | |
|---|---|---|---|---|
| R$_1$ | HSV-1 | HSV-2 | VZV | HCMV |
| (structure shown) | 18 | 18 | 18–36 | 18–36 |

TABLE 1-continued

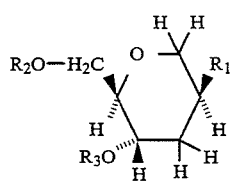

| | ID$_{50}$ ($\mu$M) for the following viruses | | | |
|---|---|---|---|---|
| R$_1$ | HSV-1 | HSV-2 | VZV | HCMV |
| (adenine-like) | 8–19 | 8–19 | 38 | 4–38 |
| (cytosine) | 0.4–0.8 | 0.4–0.8 | 4–8 | 2 |
| (5-iodouracil) | 0.3–1.4 | 3–5.4 | 68–272 | >272 |
| (thymine) | 390 | >390 | 39–390 | ≧390 |
| (5-(2-bromovinyl)uracil) | 29–72 | >288 | 5.7–14.5 | >288 |

What is claimed is:

1. A compound of the formula

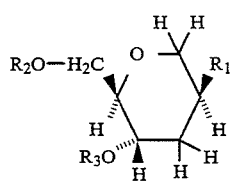

including a pharmaceutically acceptable salt therof wherein:

R$_1$ is

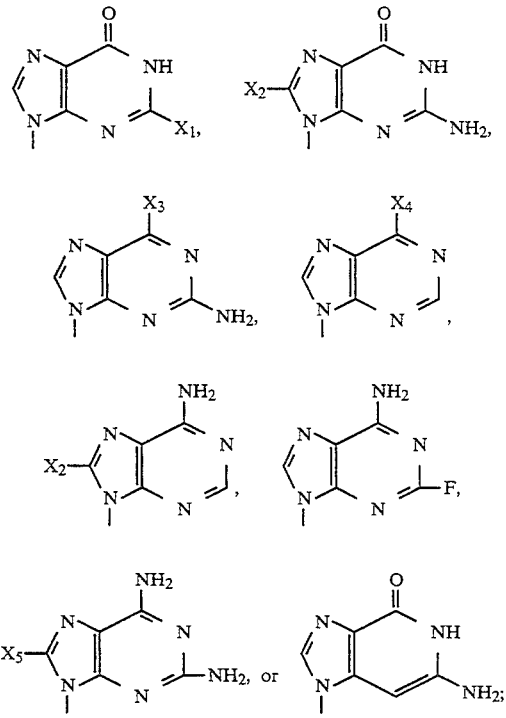

X$_1$ is hydrogen, amino,

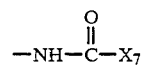

or —N═CHN (X$_8$)$_2$;

X$_2$ is methyl, fluoro, chloro, bromo, iodo, hydroxy, or amino;

X$_3$ is hydrogen, chloro, iodo, or —O—X$_8$;

X$_4$ is amino chloro,

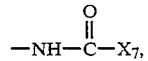

or —N═CHN(X$_8$)$_2$;

X$_5$ is hydrogen, methyl, fluoro, chloro, bromo, iodo, hydroxy or amino;

X$_7$ is hydrogen, alkyl, substituted alkyl, or aryl;

X$_8$ is alkyl;

R$_2$ and R$^3$ are independently selected from hydrogen, —PO$_3$H$_2$, and

and the term "alkyl" refers to straight and branched chain groups of 1 to 10 carbons, the term "substituted alkyl" refers to such alkyl groups having one or more substituents selected from the group consisting of chloro, bromo, fluoro, iodo, amino, azido, hydroxy, cyano, trialkylammonium (wherein each alkyl group has 1 to 6 carbons), alkoxy of 1 to 6 carbons, aryl and carboxy, and the term "aryl" refers to phenyl and phenyl substituted with one, two or three substituents selected from the group consisting of alkyl of 1 to 6 carbons, alkoxy of 1 to 6 carbons, chloro, bromo, fluoro, iodo, trifluoromethyl, amino, alkylamino of 1 to 6 carbons, dialkylamino wherein each alkyl is of 1 to 6 carbons, nitro, cyano, alkanoyloxy of 2 to 11 carbons, carboxy, carbamoyl, and hydroxy.

2. A compound of claim 1 wherein:

$R_1$ is

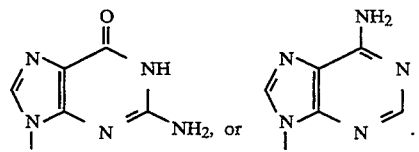

3. A compound of claim 2 wherein $R_2$ and $R_3$ are both hydrogen.

4. The compound of claim 3, [3S-(3α, 5β, 6α)]-2-amino-1,9-dihydro-9-[tetrahydro-5-hydroxy-6-(hydroxymethyl)-2H-pyran-3-yl]-6H-purin-6-one.

5. The compound of claim 3, [2R-(2α, 3β, 5α)]-5-(6-amino-9H-purin-9-yl)tetrahydro-3-hydroxy-2H-pyran-2-methanol.

6. An antiviral composition comprising a pharmaceutically acceptable carrier and an effective amount of a compound of claim 1.

7. A method of treating a viral infection in a mammalian species comprising administering an effective amount of the composition of claim 6.

* * * * *